(12) United States Patent
Swanson

(10) Patent No.: US 6,973,342 B1
(45) Date of Patent: Dec. 6, 2005

(54) FLEXIBLE BIO-PROBE ASSEMBLY

(75) Inventor: John W. Swanson, Portland, OR (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 0 days.

(21) Appl. No.: 10/822,491

(22) Filed: Apr. 12, 2004

Related U.S. Application Data

(60) Continuation of application No. 10/320,072, filed on Dec. 16, 2002, now Pat. No. 6,719,582, which is a continuation-in-part of application No. 09/653,489, filed on Aug. 31, 2000, now Pat. No. 6,495,020, which is a division of application No. 09/518,006, filed on Mar. 2, 2000, now Pat. No. 6,368,147.

(51) Int. Cl.[7] .............................................. A61B 5/04
(52) U.S. Cl. ..................... 600/378; 600/544; 607/116
(58) Field of Search ............................. 600/378, 544; 607/116

(56) References Cited

U.S. PATENT DOCUMENTS

| | | | | |
|---|---|---|---|---|
| 4,461,304 A | * | 7/1984 | Kuperstein | 600/378 |
| 5,038,781 A | * | 8/1991 | Lynch | 607/61 |
| 5,524,338 A | * | 6/1996 | Martyniuk et al. | 600/378 |
| 6,024,702 A | * | 2/2000 | Iversen | 600/378 |
| 6,171,239 B1 | * | 1/2001 | Humphrey | 600/378 |
| 6,330,466 B1 | * | 12/2001 | Hofmann et al. | 600/378 |
| 2002/0198582 A1 | * | 12/2002 | Edell et al. | 607/116 |
| 2003/0100823 A1 | * | 5/2003 | Kipke et al. | 600/378 |

* cited by examiner

Primary Examiner—Lee S. Cohen
(74) Attorney, Agent, or Firm—Law Office of Timothy E. Siegel; Timothy E. Siegel

(57) ABSTRACT

A method of producing an electrode brain probe assembly, using a flexible substrate comprising a polymeric layer bearing a conductive material coating. Photolithography and electroplating are used to form a set of contacts and conductors on the polymeric layer of the flexible substrate. Also, the flexible substrate is shaped to have a distal end and to be at least 5 mm long, but less than 5 mm wide and less than 1 mm thick.

9 Claims, 4 Drawing Sheets

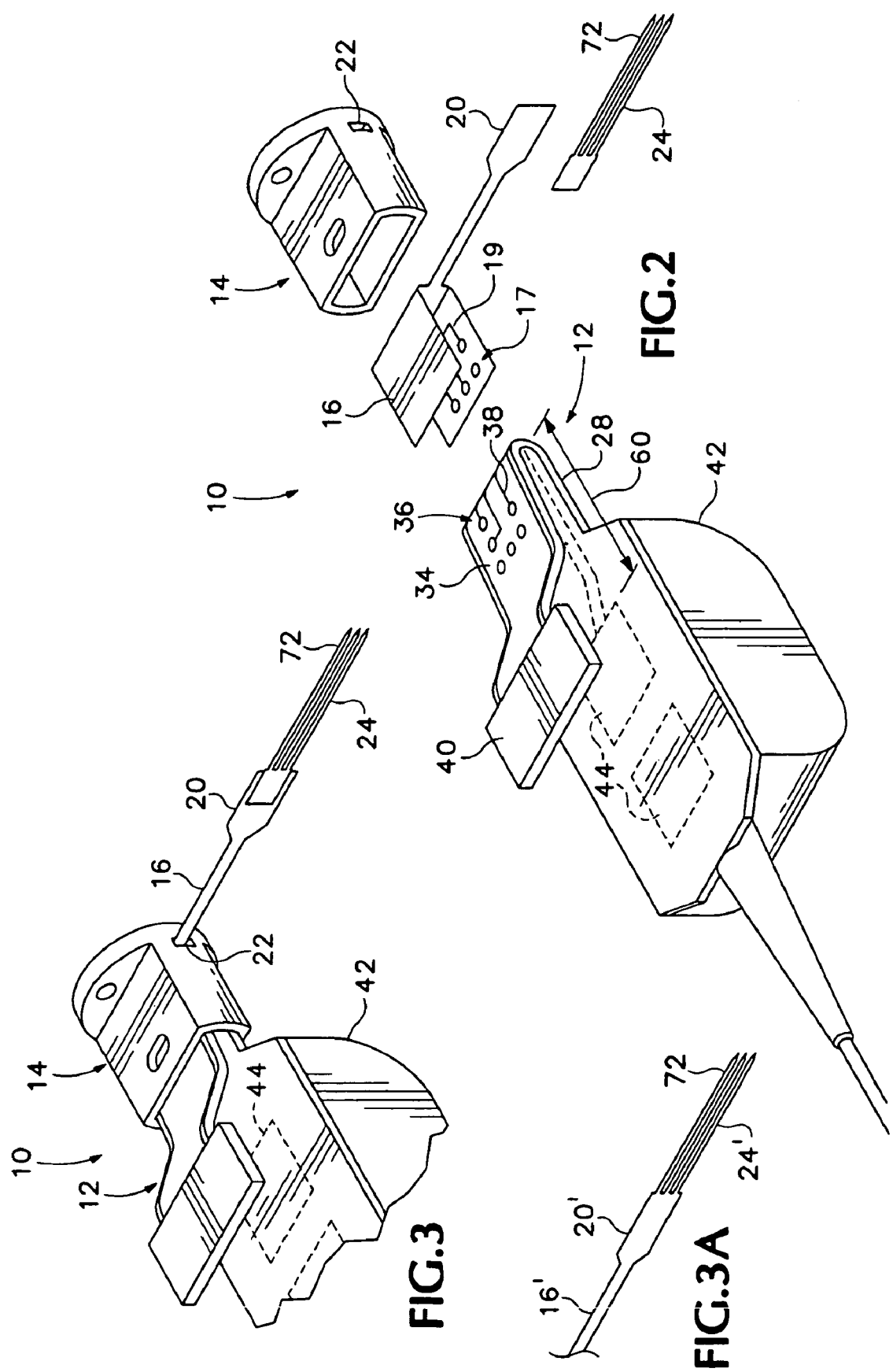

FLEXIBLE BIO-PROBE ASSEMBLY

RELATED PATENT APPLICATIONS

The present application is a continuation of application Ser. No. 10/320,072 filed Dec. 16, 2002, now U.S. Pat. No. 6,719,582, which is a continuation in part of application Ser. No. 09/653,489, filed Aug. 31, 2000, now U.S. Pat. No. 6,495,020, which is, in turn, a divisional of application Ser. No. 09/518,006, filed Mar. 2, 2000, now U.S. Pat. No. 6,368,147 issued Apr. 9, 2002.

STATEMENT OF GOVERNMENT SUPPORT

This invention was made with government support under 2R44NS33427 awarded by the SBIR. The government has certain rights in the invention.

BACKGROUND OF THE INVENTION

The present invention is a method of making a flexible brain probe assembly.

Creating a probe that contacts the brain tissue represents a challenge to researchers. Researchers typically wish to measure electrical activity at specific sites within the brain that share a well-defined physical relationship to one another. Probes produced by photolithographic techniques, such as the probe designed by personnel at the University of Michigan that is known in the industry and research community as the "University of Michigan Probe," permit the accurate placement of electrode sites that are sufficiently small to permit the measurement of electrical activity at a specific set of predefined sites within the brain. Unfortunately, the desire to use photolithography has prompted the use of silicon as a substrate. Because this material is quite brittle, the use of it creates a risk of breakage inside the brain, endangering the subject or patient and limiting the insertion strategies available to researchers. Moreover, the use of silicon prevents the University of Michigan probe from moving with the brain, which does move about slightly within the skull. In addition, silicon is subject to some restoring force, which tends to cause a silicon probe to migrate over time. Both of these drawbacks have the potential result of causing trauma to the brain tissue.

Another type of probe that is currently available includes a set of insulated wires having laser created apertures exposing electrode sites. Although this type of probe is useful for many applications, it does not yield the precision or the freedom of electrode placement that the University of Michigan probe permits.

A nerve cuff is a device for wrapping about a nerve to electrically stimulate and/or receive electric signals from the nerve. The production of nerve cuffs has also been problematic as the fine scale of the needed features has been difficult to produce on a flexible substrate capable of being wrapped about a nerve.

What is needed but not yet available is an electrode probe and method of making the same that affords unconstrained and accurate placement of the electrodes, but offers flexibility and robustness and is thereby less susceptible to breakage than currently available probes.

SUMMARY

In a first separate aspect, the present invention is a method of producing an electrode bio-probe assembly, using a flexible substrate comprising a polymeric layer bearing a conductive material coating. Photolithography and electroplating are used to form a set of contacts and conductors on the polymeric layer of the flexible substrate. Also, the flexible substrate is shaped to have a distal end and to be greater than 5 mm long, less than 5 mm wide and less than 1 mm thick.

In a second separate aspect, the present invention is a method of producing a nerve cuff assembly for application to a target nerve. The method includes the use of photolithography and electroplating to form a set of contacts and conductors on the polymeric layer of a flexible substrate having a polymeric layer and bearing a conductive material coating. The flexible substrate is sized and shaped to fit about the target nerve.

The foregoing and other objectives, features and advantages of the invention will be more readily understood upon consideration of the following detailed description of the preferred embodiment(s), taken in conjunction with the accompanying drawings.

BRIEF DESCRIPTION OF THE DRAWINGS

FIG. 2 is an exploded perspective view of a connector according to the present invention.

FIG. 3 is a perspective view of the connector of FIG. 1, with the two connector halves mated.

FIG. 3A is a perspective of a portion of an alternative embodiment to FIG. 1, showing the differing structure of the alternative embodiment.

DETAILED DESCRIPTION OF THE PREFERRED EMBODIMENT

Figure 1:
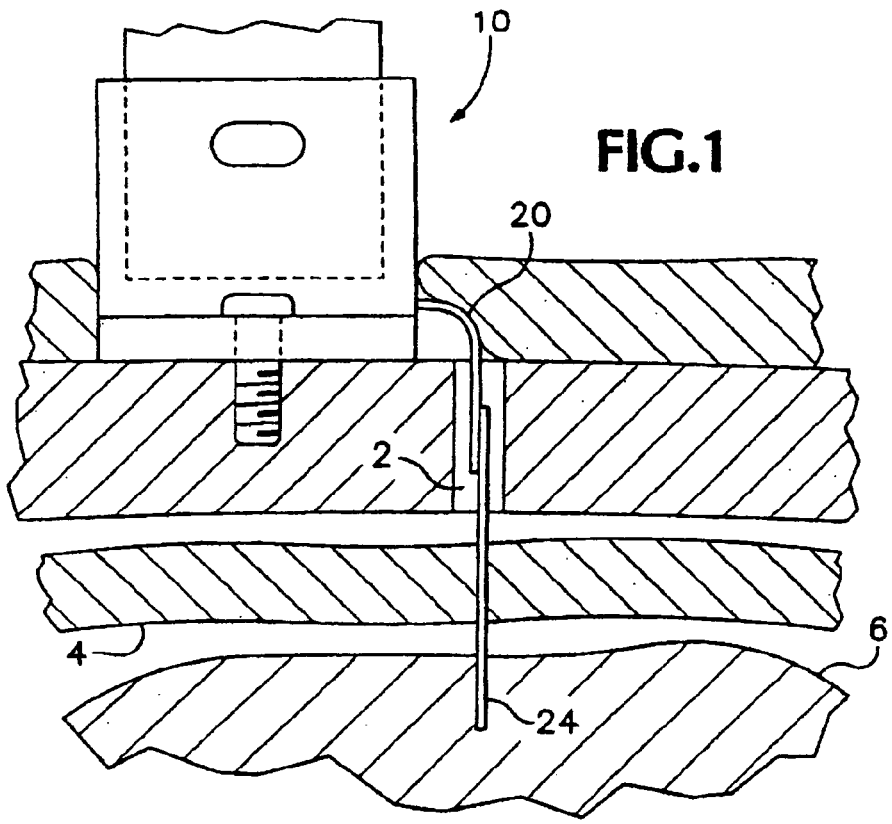
FIG. 1 is a side view of the connector of FIG. 1, shown attached to a skull and connected to a brain probe that is embedded in brain tissue.
Figure 4:
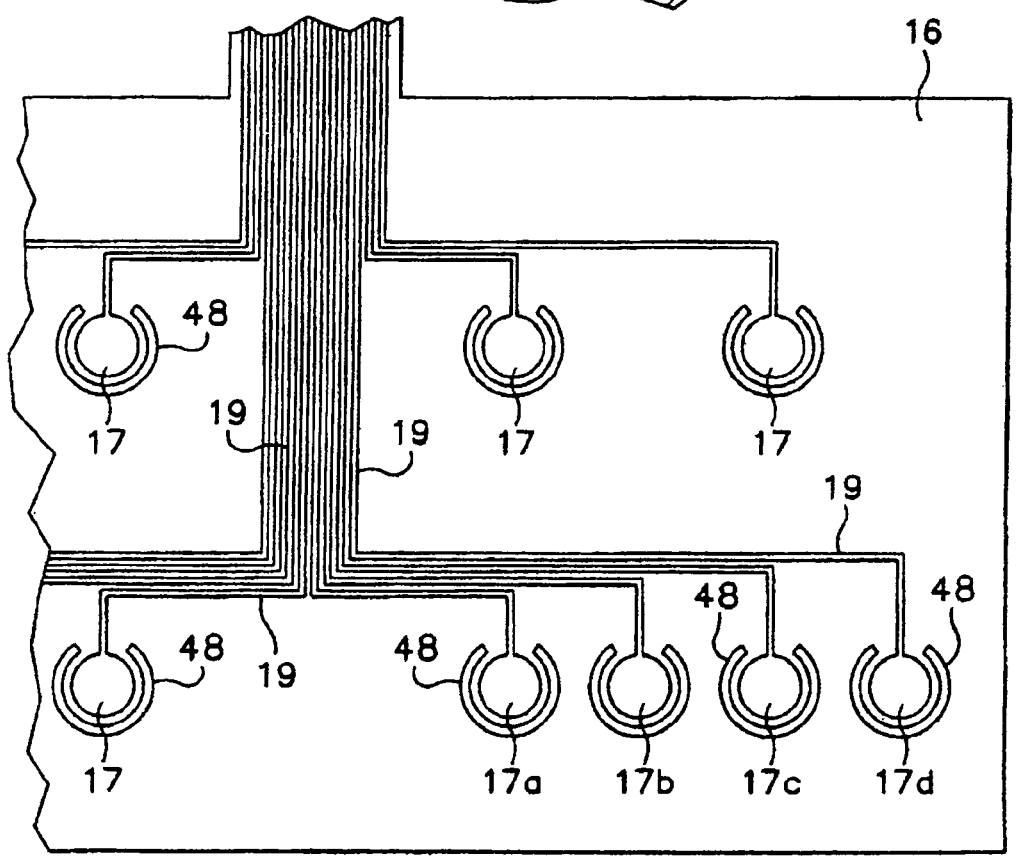
FIG. 4 is a greatly expanded plan view of a connective surface of the connector of FIG. 1.

Referring to FIG. 1, a percutaneous connector 10 is screwed into the skull 1 and is connected, by way of a multi-conductor microcable 20, to a brain probe 24 that passes through an aperture 2 in the skull, through the dura 4 (and into the brain 6), for measuring brain activity at a specific set of points.

Referring to FIGS. 2, 3 and 3A a percutaneous connector 10 according to the present invention includes a male-half 12, a female-half bracket 14 and a female-half flex circuit (or flexible polymer) connective assembly 16 bearing a set of contacts 17 and conductive traces 19. A multi-conductor microcable 20 forms a portion of assembly 16 and is threaded through an aperture 22 in bracket 14. The microcable 20 attaches to and extends traces 19 to brain probe 24. As shown in FIG. 3a in an alternative embodiment, a connective assembly 16' includes a microcable 20' that includes a brain probe 24' as a unitary part of its construction. The male-half includes a resilient clip portion 28, the exterior of which is covered with a flex-circuit 34 bearing a set of contacts 36 (matching the arrangement of contacts 19) and conductive traces 38.

A first prong 40 and a second prong 42, which is physically coincident with an op-amp housing, partially defines clip portion 28. A user can grasp male-half 12 by the first and second prongs 40 and 42 to squeeze these prongs 40 and 42 together. The male-half 12 can then be inserted into the female-half 14, without exerting pressure against female-half 14, which could cause pain or tissue trauma to the patient or test subject. Finally, the user releases prongs 40 and 42 so that the resiliency of clip 28 will force each exterior side of clip 28, and therefore contacts 36, to touch the contacts 17 in female-half 14.

Referring to FIGS. 4 and 5a–5g, contacts 17 and traces 19 are made of conductive material, such as a metal (copper, gold or sliver) or a conductive polymer that has been deposited and etched on top of a laminate having a layer of dielectric substrate 50 and a base layer silicone 70 or some other biocompatible, compliant material. Semicircular isolation cuts 48 through the layers 50 and 70 (in an alternative preferred embodiment only layer 50 is cut through by the laser) positionally decouple a first contact 17a from neighboring contacts 17b, 17c and 17d, permitting contact 17a to be depressed into the spongy layer of silicone 70 without pulling down the neighboring contacts 17b, 17c and 17d. This independent depressability causes the protrusional misalignment of contacts 17 and 36 to be forgiven.

The miniature scale that is made possible by the use of photolithography and flex circuit technology, as described above, facilitates a further advantage that may be realized as part of the present invention. This is the placement of op amps in extremely close proximity to contacts 36. For connectors in which the contacts are spread apart from each other, it is necessary to gather together conductive paths from all the different contacts prior to sending them all to a set of op amps. Because contacts 36 are all so close together, traces 38 are routed to a set of op amps 44, that are about 0.5 cm away and are housed in the second prong 42, which doubles as an op amp housing. As a result, signal line noise and cross talk are minimized.

Figure 5A:
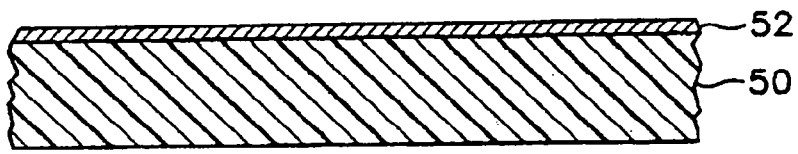
FIGS. 5a–5g is a series of greatly enlarged side cross-sectional views showing the construction of the connector flex circuit, or thin film, which may include the brain probe flex circuit of FIG. 1 in a single unit.
Figure 5B:
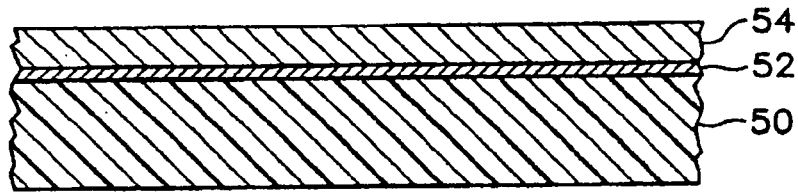
Figure 5C:
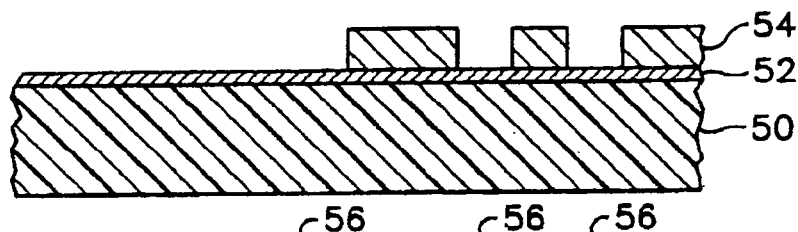
Figure 5D:
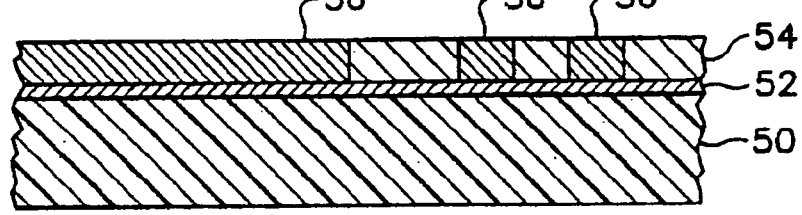
Figure 5E:
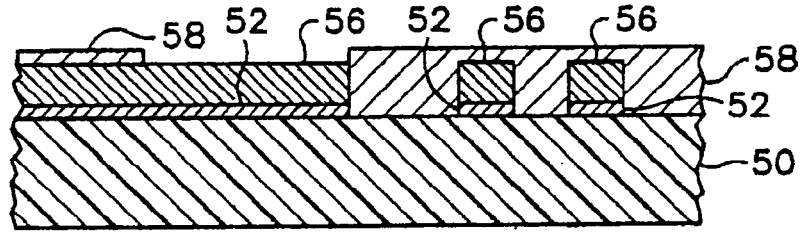
Figure 5F:
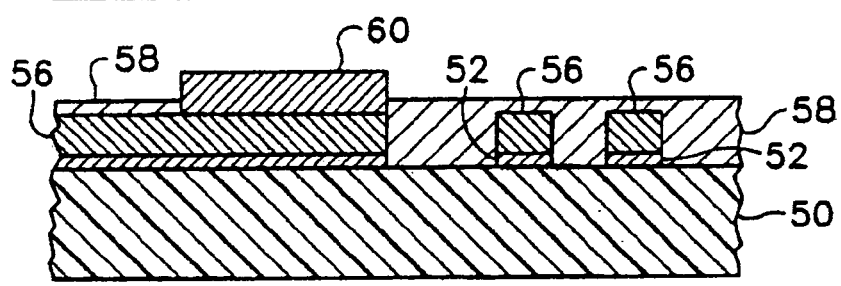
Figure 5G:
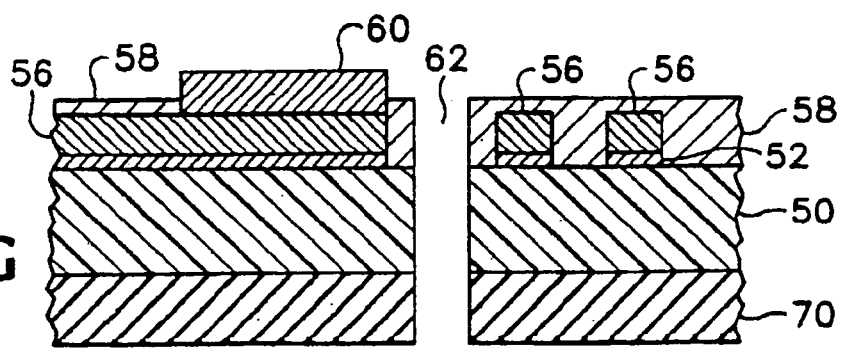

Referring to FIGS. 5a–5g, the photolithography process for making the brain probe 24 and the contacts of the percutaneous probe contact structure 30 are quite similar, except that different materials may be used and the percutaneous probe contact structure 30 includes a base layer of silicone 70, that is only shown in FIG. 5g, for the sake of simplicity. Referring specifically to FIG. 5a, the photolithography process begins with a layer of dielectric substrate 50, the composition of which is discussed below, that is coated with a base layer of conductive material 52, such as a titanium-gold-titanium sandwich. FIG. 5b shows the structure of FIG. 5a, which at this point has been covered with a layer of photo resist material 54, typically applied by spin-coating. FIG. 5c shows the effect of exposing the photo resist material to a pattern of light and washing off the exposed (or not exposed if a negative process is used) material with a developing agent. Next, as shown in FIG. 5d, additional conductive material (typically copper) is built up on the exposed base layer 52, typically through electrolysis. As shown in FIG. 5e, the remaining photo resist material 54 is washed off with a solvent and a layer of dielectric (and permanent) photo resist 58 is applied and patterned, via exposure to a pattern of light and subsequent washing with a developing agent or solvent. Then, additional electrolytic plating is performed (FIG. 5f) to create a contact 60 and the substrate is cut with an nd:YAG laser to form a kerf or cut 62. When the process shown in FIGS. 5a–5g is for producing connector 10, cut 62 is the same as isolation cut 48. When the process shown in FIGS. 5a–5g is for producing a brain probe 24, cut 62 separates a first brain probe 24 from a wafer or thin plastic film upon which several brain probes have been etched. In contrast to the situation with respect to silicon, which may be separated by etching, it appears that no etching process has been developed for cutting the materials used for substrate 50, which are discussed below.

The dielectric substrate 50 that is used for the brain probe 24 is preferably a polymer material having a high glass transition temperature, high tensile strength and low elasticity. More specifically, substrate 50 may be made of polyether sulfone, polyimide or other material having the desired characteristics. If polyimide is used, it should be coated or treated so that it does not dissolve in the body's interstitial fluid, or used for a probe that is not to be implanted for long enough for the polyimide to dissolve. Photo resist material 54 may be a photosensitive acrylate, polyether or polyurethane, preferably having a high molecular weight. Permanent photo resist 58 may be a permanent polyimide, a type of material that is widely available from well-known photo resist companies. These companies typically sell a wet etch agent specifically designed to etch each permanent polyimide photo resist that they sell.

Brain probe 24 includes three prongs 72. Each prong 72 is on the order of 15 mm long, 3 mm wide and 0.3 mm thick. During the manufacturing process each prong 72 is sharpened so that it may more easily be driven through the brain tissue. It is desirable that a brain probe, if it is to be implanted for a period of time on the order of weeks, be very pliable, so that it may conform to the brain tissue surrounding it and not cause further damage by pressing against the delicate brain tissue. If the brain probe is to be installed by being driven through brain tissue, however, it must be fairly rigid, requiring a strength layer, such as layer of steel or some other resilient material, laminated beneath layer 70, typically before the production process begins.

Figure 6:
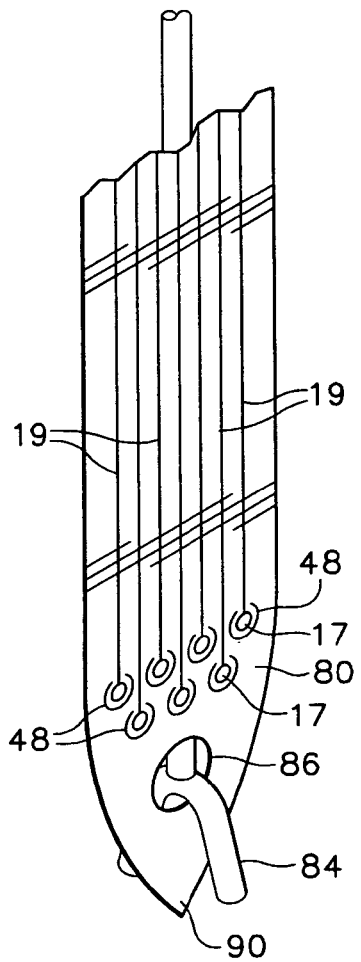
FIG. 6 shows an expanded flexible brain probe, according to the present invention, and a tool for pushing this brain probe through brain tissue, also according to the present invention.
Figure 7:
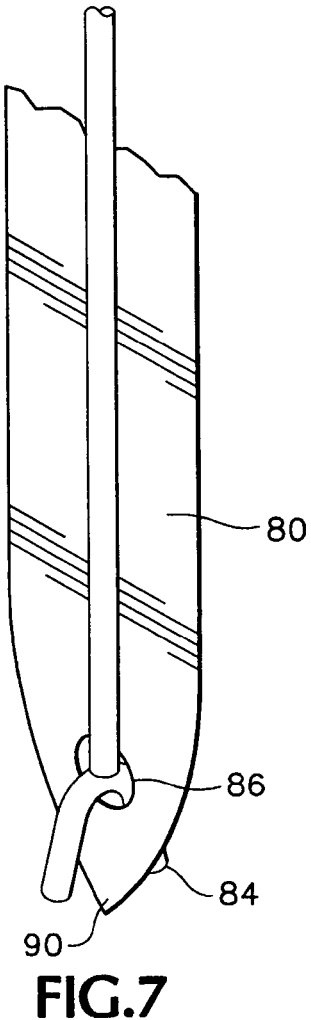
FIG. 7 shows the flexible brain probe and tool of FIG. 6, in a 180° rotated view.

Referring to FIGS. 6 and 7, in one preferred embodiment a brain probe 80 is constructed to be very pliable. In brain probe 80 only a single point 90 is provided, in order to facilitate the placement process, which is complicated by the three-pointed (or pronged) embodiment shown in FIG. 3. FIG. 6 shows brain probe 80 in tandem with a placement tool 84, which engages brain probe 80 at aperture 86. Placement tool 84 is used to push the point of probe 80 through brain tissue 6 (FIG. 1), to the point at which contact with brain tissue 6 is desired. For chronically implanted brain probes, the quality of being pliable may be very important, to avoid the damage that a rigid brain probe could inflict with patient movement. The brain moves about in the skull with patient head movement, and colliding with a rigid probe could easily damage the soft brain tissue.

In the embodiment of FIG. 6, electrodes 17 are from 12.56 square microns to 300 microns in surface area. In one preferred embodiment electrodes 17 are 176 have a surface area of 176 square microns. The probe 80, itself is at least 5 mm long, and no more than 5 mm wide and 1 mm thick. In the preferred embodiment shown, cuts 48 are through-cuts and permit tissue ingrowth, which along with the tissue ingrowth at aperture 86 helps to anchor brain probe 90, in the brain tissue. In an alternative preferred embodiment, cuts 48 are not present.

Figure 8:
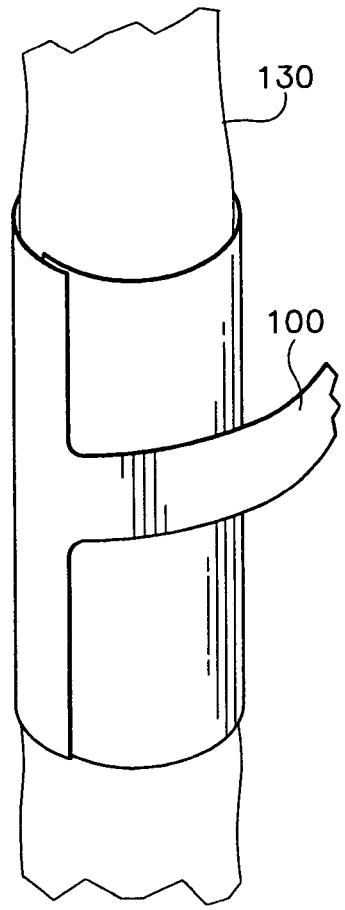
FIG. 8 shows a nerve cuff produced in accordance with the present invention, wrapped about a nerve.
Figure 9:
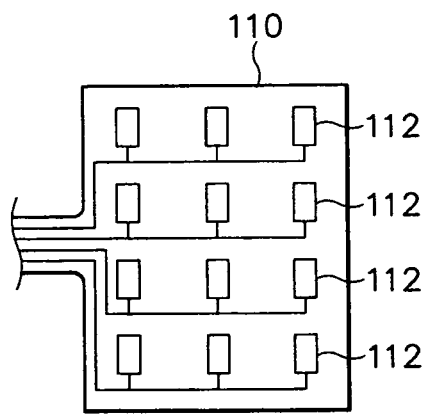
FIG. 9 shows a nerve cuff produced in accordance with the present invention.
Figure 10:
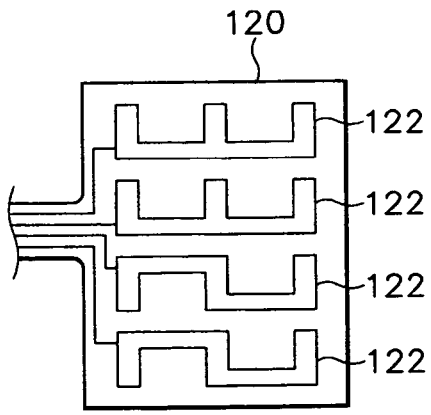
FIG. 10 shows an alternative embodiment of a nerve cuff produced in accordance with the present invention.

Referring to FIGS. 8, 9 and 10, the method of construction shown in FIGS. 5a–5g is used for the production of nerve cuffs 100, 110 and 120. A nerve cuff is a device that is adapted to be wrapped around a nerve 130 and used to electrically stimulate the nerve 130. In nerve cuff 110 a set of twelve contacts 112 have been created through photolithography. In nerve cuff 120 four complex contacts 122, designed for circumferentially contacting a nerve have been created by way of photolithography.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. An electrode brain probe assembly, comprising:
    a) a flexible polymeric substrate;
    b) a set of electrical contacts and conductors on said flexible polymeric substrate; and
    c) said electrode brain probe assembly having a distal end, and being greater than 5 mm long, less than 5 mm wide and less than 1 mm thick.

2. The assembly of claim 1 further being pointed at said distal end.

3. The assembly of claim 1 further defining a through hole at said distal end, thereby permitting the use of a placement device to push said bio-probe into delicate soft tissue.

4. The assembly of claim 1 wherein said flexible polymer substrate is comprised of a layer of polyether sulfone.

5. The assembly of claim 1 wherein said flexible polymer substrate is comprised of a layer of polyimide.

6. The assembly of claim 1 wherein said conductors are made of a metal.

7. The assembly of claim 1 wherein said conductors are made of a conductive polymer.

8. The assembly of claim 1 wherein said flexible polymer substrate is comprised of a layer of liquid crystal polymer.

9. The assembly of claim 3 wherein said delicate soft tissue is brain tissue.

* * * * *